United States Patent
Dente et al.

(10) Patent No.: US 11,065,357 B2
(45) Date of Patent: Jul. 20, 2021

(54) WATER DISPERSIBLE FRAGRANCED FILM AND USE THEREOF

(71) Applicant: Robertet, Inc., Budd Lake, NJ (US)

(72) Inventors: Stephen V. Dente, Budd Lake, NJ (US); Inga Verbicka, Budd Lake, NJ (US); Ralph Gencarelli, Budd Lake, NJ (US); Ben Fundaro, Budd Lake, NJ (US)

(73) Assignee: ROBERTET, INC., Budd Lake, NJ (US)

( * ) Notice: Subject to any disclaimer, the term of this patent is extended or adjusted under 35 U.S.C. 154(b) by 106 days.

(21) Appl. No.: 16/255,183

(22) Filed: Jan. 23, 2019

(65) Prior Publication Data
US 2019/0224358 A1 Jul. 25, 2019

Related U.S. Application Data

(60) Provisional application No. 62/621,950, filed on Jan. 25, 2018.

(51) Int. Cl.
| | | |
|---|---|---|
| *A61L 9/05* | (2006.01) | |
| *A61L 9/04* | (2006.01) | |
| *C11D 17/04* | (2006.01) | |
| *C11D 3/50* | (2006.01) | |
| *C11D 3/37* | (2006.01) | |

(52) U.S. Cl.
CPC ............. *A61L 9/042* (2013.01); *A61L 9/05* (2013.01); *C11D 3/3753* (2013.01); *C11D 3/505* (2013.01); *C11D 17/042* (2013.01)

(58) Field of Classification Search
CPC ... A61L 9/01; A61L 9/04; A61L 9/042; A61L 9/044; A61L 9/048; A61L 9/05; C11D 3/3753; C11D 3/505; C11D 17/042; C11D 17/043
See application file for complete search history.

(56) References Cited

U.S. PATENT DOCUMENTS

2017/0216166 A1\* 8/2017 Sasaki .................... C11D 3/505

FOREIGN PATENT DOCUMENTS

EP 0728804 A1 8/1996

OTHER PUBLICATIONS

International Search Report for corresponding application PCT/US2019/014711 dated Mar. 21, 2019.
Fan, Y., et al: "Modulation of partition and localization of perfume molecules in sodium dodecyl sulfate micelles ", Soft Matter, vol. 12, No. 1, Jan. 1, 2016, pp. 219-227.

\* cited by examiner

*Primary Examiner* — Timothy C Cleveland
(74) *Attorney, Agent, or Firm* — Norris McLaughlin PA

(57) ABSTRACT

Fragranced films containing a water soluble a/o water dispersible polyvinyl alcohol polymer are disclosed. Uses of the fragranced films in providing a fragrance benefit and/or in controlling malodours is also disclosed, including when used in conjunction with lavatory appliances, dishwashing machines and in laundry washing machines.

12 Claims, No Drawings

WATER DISPERSIBLE FRAGRANCED FILM AND USE THEREOF

This application claims priority to U.S. 62/621,950 filed 25 Jan. 2018.

The present invention relates to fragrance containing water dispersible films, methods for their production and uses thereof.

Malodors are all too frequently and undesirably encountered in certain environments, such as in lavatories and the like. Such malodors may be caused by any variety of sources, including but not limited to; improperly cleaned lavatory appliances and/or residues of human waste in lavatory appliances such as toilets, urinals, and the like. Such residues typically harbor undesired microorganisms which are not only unhygienic, but which are also malodorous. While improved cleaning regimens drastically reduce the incidence of such malodors, such is not always sufficiently frequently a/o satisfactorily performed. Such has induced the art to provide a plethora of devices and/or compositions are known in order to ameliorate these effects.

Without limitation, prior art devices include those which are used in the proximity of lavatory appliances, or are used within lavatory appliances themselves. Such devices typically include a liquid, solid or gel composition which include one or more surfactants, a fragrance composition, and optionally a bleach constituent or other sanitizing agent, colorants and further optional constituents. Such devices typically include or elements which are used to retain the aforesaid liquid, solid or gel compositions in suitable position in the proximity of, or within the device. Certain known art devices include viscous compositions which contain one or more fragrances which are applied to a surface of a lavatory appliance upon which they are retained after the device used to apply or dispense it is removed. Also known to the prior art are sprays, including pressurizable liquid sprays which may be dispensed using a pump such as a manually operable pump, as well as aerosol compositions. Such may be used in various manners; in a simple form, a pressurized aerosol container is placed on a surface within the near proximity of the lavatory appliance, from which is quantity of the composition may be dispensed by a person using the lavatory appliance when deemed necessary in order to counteract or mask the malodor. Also known are dispensing devices which deliver a spray containing a fragrance composition, which are operated automatically or semiautomatically. In one known embodiment, a pressurized aerosol container is operatively associated with a dispensing device which in response to a periodic time interval and/or in response to one or more sensors which sample air quality in the near proximity of the device, functions to release a dose of an air treatment composition from the aerosol container. Further devices which dispense a spray also include those in which a fragrance containing liquid within a refill container is dispensed into the ambient environment, such as by evaporation without heating or evaporation which is aided by a heat source to accelerate the rate of evaporation, or by electromechanical means such as an oscillating microperforated disk which entrains micro droplets of the fragrance containing liquid and disperses them into the ambient environment. Also known are so-called "static" air treatment devices, which may include a reservoir containing a quantity of a fragrance containing liquid, a fragrance containing semi-solid (i.e. a gel) or a solid from which a fragrance volatilizes without requiring any powered device or heat source.

While such devices and compositions are known to the art, they are not without shortcomings. For examples, many of the aforesaid devices are complicated, and costly. Sprayable compositions, including those dispense from pressurized aerosols or via microperforated disks might be undesirable as the relatively small particle size of the droplets being dispensed by such devices might pose an inhalation risk. So called static air treatment devices may be difficult to position in the proximity of a lavatory appliance. Thus, there remains a real need in the relevant art for improved articles, methods of making such articles, and methods of using such improved articles which are effective in the treatment of malodors.

It is to such and further objects that the current invention relates.

In a first embodiment of the present invention there is provided a water-soluble or water dispersible film primarily comprising a water soluble polyvinyl alcohol composition, a fragrancing composition, and optionally one or more further materials, preferably at least a thickener constituent, and an organic solvent constituent. In preferred embodiments, the fragrancing composition is adsorbed and/or absorbed onto/into a carrier substance, which is preferably a micronized material which allows a relatively even distribution within the dispersible film.

A second embodiment of the present invention, there is provided a method for the manufacture of a water-soluble or water dispersible film primarily comprising a water soluble polyvinyl alcohol composition, a fragrancing composition, and optionally one or more further materials, preferably at least a thickener constituent, and an organic solvent constituent. In preferred embodiments, the fragrancing composition is adsorbed and/or absorbed onto/into a carrier substance, preferably a micronized material which allows for a relatively even distribution within the dispersible film. The method includes the step of combining the essential constituents with the polyvinyl alcohol and subsequently forming a film thereof, such as by casting according to a continuous or discontinuous process.

In a third embodiment of the present invention, there is provided a method for the treatment of and/or the amelioration of undesired malodors emanating from, or in the near proximity of a lavatory appliance, which method comprises the step of:

providing to water present within or in the proximity of a lavatory appliance a water-soluble or water dispersible film primarily comprising a water soluble polyvinyl alcohol composition, a fragrancing composition, and optionally one or more further materials, preferably at least a thickener constituent, and an organic solvent constituent; in preferred embodiments, the fragrancing composition is adsorbed and/or absorbed onto/into a carrier substance, which is preferably a micronized material.

In a fourth embodiment of the present invention, there is provided a method for the treatment of and/or the amelioration of undesired malodors emanating from, or in the near proximity of a kitchen appliance, which method comprises the step of:

providing to water present within or in the proximity of a kitchen appliance a water-soluble or water dispersible film primarily comprising a water soluble polyvinyl alcohol composition, a fragrancing composition, and optionally one or more further materials, preferably at least a thickener constituent, and an organic solvent constituent; in preferred embodiments, the fragrancing composition is adsorbed and/or absorbed onto/into a carrier substance, which is preferably a micronized material.

In a fifth embodiment of the present invention, there is provided a method for the treatment of and/or the amelioration of undesired malodors emanating from, or in the near proximity of a laundry appliance, which method comprises the step of:

providing to water present within or in the proximity of a lavatory appliance a water-soluble or water dispersible film primarily comprising a water soluble polyvinyl alcohol composition, a fragrancing composition, and optionally one or more further materials, preferably at least a thickener constituent, and an organic solvent constituent; in preferred embodiments, the fragrancing composition is adsorbed and/or absorbed onto/into a carrier substance, which is preferably a micronized material.

Further objects and embodiments of the present invention are discussed further in this patent application.

The present inventor had surprisingly found that fast dissolving films providing a pronounced and beneficial release of fragrance to the ambient environment are those films based on water soluble a/o water dispersible polyvinyl alcohol polymer which is dissolvable or dispersible in water which contain a fragrance constituent, the fragrance constituent comprising one or more components, the total amount of which do not exceed about 10% wt. of the total mass of the fragrance constituent, wherein these said components are characterized in that each individually concurrently satisfies the following parameters: (a) a c Log P<3.00; (b) a Vapor Pressure >0.1 mm Hg; (c) a molecular weight of <180. These parameters may be evaluated using conventional analytical methods in order to determine the suitability of incorporating a fragrance composition in a fast dissolving film of the invention. The inventors have found that fragrance constituents which omit, or which include more than about 10% wt. of one or more of the said constituents which meet these three concurrent parameters do not meet the required film dissolution, fragrance delivery and malodour counteracting features of fast dissolving films of the present invention. Certain particularly preferred embodiments, as well as comparative examples of films are disclosed in the examples, below.

The inventors have surprisingly found that the fragrance perception, or "bloom", that is to say the long term (i.e., 5 minutes, 10, minutes, 15 minutes, 20 minutes, 25 minutes, 30 minutes, and time intervals greater than the above) olfactory perception of the fragrance constituent in a headspace can be realized by the use of relatively small amount of components of a fragrance constituent where these components satisfy the concurrent parameters: (a) a c Log P<3.00; (b) a Vapor Pressure >0.1 mm Hg; (c) a molecular weight of <180. Such is unexpected from the prior art which does not teach such concurrent parameter, or that relatively low amounts of the individual constituents need be present in a fragrance constituent.

In preferred embodiments, the predominant constituent of the fragranced films of the invention is a water soluble a/o water dispersible polyvinyl alcohol polymer which is dissolvable or dispersible in water, preferably at temperatures of between about 10° C.-50°. Preferably at least about 90% of the mass of the fragranced films are dissolved within 15-120 seconds after being contacted with sufficient water; such dissolution may be at water temperatures of 10° C., 20° C., and/or 50°. Preferred formulations include those which have faster dissolution times, i.e, about 30 seconds or less after being contacted with sufficient water.

The polyvinyl alcohol polymer may be a polyvinyl alcohol polymer formed substantially of (at least 90%, preferably at least 95% of) polyvinyl alcohol monomers, or may be a copolymer containing at least 75% of polyvinyl alcohol monomers, with further monomers. The polyvinyl alcohol polymer may be formed from at least partial hydrolysis of polyvinylacetate monomers to form a polyvinylacetate polymer which can be generally represented in the following structure (I):

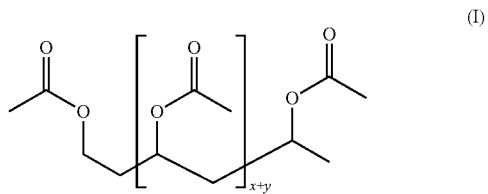

which can then be subjected to hydrolysis to form a polyvinyl alcohol having few, acetyl moieties as illustrated in the following structure (II):

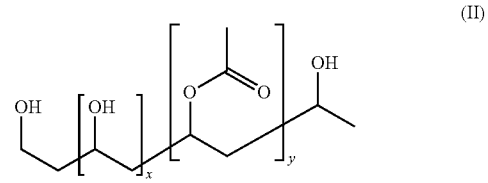

in which each of x and y are integer values, such that the ratio of x:y is at least 3:1, preferably (in order of increasing preference) at least 4:1, 5:1, 7.5:1, 10:1, 15:1, 20:1, 25:1, 50:1, 90:1 95:1, 99:1 999:1, and that the polymer has a number average molecular weight of between about 5,000 and about 500,000, more preferably of at least 10,000 and not more than about 1,000,000, but preferably not more than about 500,000, 475,000, 450,000, 425,000, 400,000, 375,000, 350,000, 325,000, 300,000, 275,000, 250,000, 225,000, 200,000, 175,000, 150,000, 125,000, 100,000 and 75,000. Polyvinyl alcohol polymers with higher degrees of hydrolysis are preferred.

It is also contemplated that as useful polyvinyl alcohol polymers are those illustrated in structure (II), in which other co-monomers other than the depicted vinylacetate monomers are present, or which are additionally present with vinylacetate monomers.

Most preferably the polyvinyl alcohol polymer contains no more than 0.1% of moieties other than vinyl alcohol moieties and thus, can be generally represented by the following structure (III):

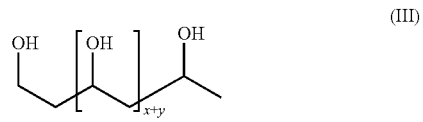

in which each of x and y are integer values, such that the polyvinyl alcohol polymer has a number average molecular weight of the polymer has a number average molecular weight of between about 5,000 and about 500,000, more preferably of at least 10,000 and not more than about 1,000,000, but preferably not more than about 500,000, 475,000, 450,000, 425,000, 400,000, 375,000, 350,000, 325, 000, 300,000, 275,000, 250,000, 225,000, 200,000, 175,000, 150,000, 125,000, 100,000 and 75,000.

The water soluble polyvinyl alcohol polymer is often the predominant constituent in the fragranced films. Preferably the water soluble polyvinyl alcohol polymer comprises at least 35% wt., preferably (in % wt.) at least 40%, 45%, 50%, 55%, 60%, 65%, 70%, 75%, 80%, 85%, 90%, 91%, 92%, 93%, 94%, 95%, 96%, 97%, 98%, and 99% wt. of the fragranced film of which it forms a part. Preferred embodiments comprise between about 45% wt.-85% wt., preferably between about 50% wt.-80% wt. and especially preferably between about 55% wt. and 70% wt. of the water soluble polyvinyl alcohol polymer constituent.

A next essential constituent is a fragrance constituent, which may include one or more components of which may be based on natural and/or synthetic fragrances and most commonly are mixtures or blends of a plurality of such fragrances, optionally in conjunction with a carrier such as an organic solvent or a mixture of organic solvents in which the fragrances are dissolved, suspended or dispersed. The fragrance constituent comprises one or more such raw materials, or components (usually a plurality of such) which when combined provide the fragrance constituent. By way of non-limiting example, natural fragrances include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamon, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of fragrance compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, .alpha.-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different fragrance compounds which, together, produce an agreeable fragrancing effect. Other suitable fragrances include essential oils, preferably essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, labolanum oil and lavendin oil.

Further components useful in forming the fragrance constituent include materials disclosed in reference texts such as the book by S. Arctander, Perfume and Flavor Chemicals, 1969, Montclair, N.J., USA, or its more recent versions, or in other works of a similar nature, such as thegoodscentcompany.com and Leffingwell websites, as well as in the abundant patent literature. Non-limiting examples of such include: essential oils and extracts, alcohols, aldehydes, ketones, esters, lactones and macrocylic compounds which provide a fragrancing benefit.

The fragrance constituent can be optionally provided in an encapsulated, or microencapsulated; in such an instance, the necessity of a carrier substance is reduced, and some instances may be omitted.

The fragrance constituent may be present in any effective amount such that it can be discerned by a consumer of the fragranced film, however is advantageously present in amounts of up to about 60% wt., preferably in an amount of at least about 0.001% wt., to at least about 50% wt. Alternately the fragrance constituent forms at least 0.5% wt. of the fragranced film, and not in excess of about (in % wt.) 50%, 49%, 48%, 47%, 46%, 45%, 44%, 43%, 42%, 41%, 40%. 39%, 38%, 37%, 36%, 35%, 34, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7.5%, 7%, 6.5%, 6%, 5.5%, 5%, 4.5%, 4%, 3.5%, 3%, 2.5%, 2%, 1.5% and 1% wt. In certain preferred embodiments, the fragrance constituent is preset in an amount of at least about 10% wt., more preferably of at least about (in % wt.) 11%, 12%, 13%, 14%, 15%, 16%, 17%, 18%, 195, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59% and 60% wt. Especially preferably the fragrance constituent is present in amounts of from about 0.001% wt. to about 45% wt., and most preferably is present in an amount of from about 10% wt. to about 40% wt. based on the total weight of the fragranced film of which it forms a part.

The inventors have surprisingly found that that the preferred embodiments include a high percentage of the fragrance constituent, and generally, amounts of at least about 10% wt, 15% wt., 20% wt., 25% wt., 30% wt., 35% wt., 40% wt. and even higher amounts are possible in the fragrance film compositions. Such is unexpected, as typically higher amounts of fragrances in a water soluble and/or water dispersible films such as those described herein might have been expected to unduly compromise the structural integrity of such films, rendering them unsuitable for use in many applications, including their use in forming water-soluble pouches or sachets which contain further constituents, or in forming self-adhering films which may be applied to water wetted surfaces, e.g, wetted surfaces of lavatory appliances such as the interior surfaces of toilet bowls, urinals, bidets, shower stalls and surfaces, bathtubs, and the like.

As noted, previously the fragrance constituent comprises one or more components, which must be present but which cumulatively not to exceed about 10% wt. of the total mass of the fragrance constituent, wherein these said components are characterized in that each concurrently satisfies the following parameters: (a) a c Log P<3.00; (b) a Vapor Pressure >0.1 mm Hg; (c) a molecular weight of <180. So, the fragrance constituent necessarily comprises at least one of said components which satisfy the foregoing parameters. Advantageously the said components comprise at least 0.001% wt, 0.01% wt., 0.05% wt., 0.1% wt., 0.2% wt., 0.3% wt, 0.4% wt., 0.5% wt., 0.75% wt., 1% wt., 1.25% wt., 1.5% wt., 1.75% wt., 2% wt., 2.25% wt., 3% wt., 3.25% wt., 3.5% wt., 3.75% wt., 4% wt., 4.25% wt., 4.5% wt., 5% wt., 5.25% wt., 5.5% wt., 5.75% wt., 6% wt., 6.25% wt., 6.5% wt., 6.75% wt., 7% wt., 7.25% wt., 7.5% wt., 7.75% wt., 8% wt., 8.25% wt., 8.5% wt., 8.75% wt., 9% wt., 9.25% wt., 9.5% wt., and 10% wt., with particularly preferred amounts of the fragrance constituent being demonstrated in one or more of the examples. Advantageously the said components which meet the foregoing parameters (a0, (b), (c) are present in the fragrance constituent within a range of two of the foregoing amounts recited immediately above.

The fragranced films optionally but particularly preferably also comprise a thickener constituent, which may, be for example, polysaccharide polymers selected from cellulose, alkyl celluloses, alkoxy celluloses, hydroxy alkyl celluloses, alkyl hydroxy alkyl celluloses, carboxy alkyl celluloses, carboxy alkyl hydroxy alkyl celluloses, naturally occurring polysaccharide polymers such as xanthan gum, guar gum, locust bean gum, tragacanth gum, or derivatives thereof, gum Arabic, polycarboxylate polymers, polyacrylamides, clays, and mixtures thereof.

Examples of the cellulose derivatives include methyl cellulose ethyl cellulose, hydroxymethyl cellulose hydroxy ethyl cellulose, hydroxy propyl cellulose, carboxy methyl cellulose, carboxy methyl hydroxyethyl cellulose, hydroxypropyl cellulose, hydroxy propyl methyl cellulose, ethylhydroxymethyl cellulose and ethyl hydroxy ethyl cellulose.

Exemplary polycarboxylate polymers thickeners have a molecular weight from about 500,000 to about 4,000,000, preferably from about 1,000,000 to about 4,000,000, with, preferably, from about 0.5% to about 4% crosslinking. Preferred polycarboxylate polymers include polyacrylate polymers including those sold under trade names Carbopol®, Acrysol® ICS-1 and Sokalan®. The preferred polymers are polyacrylates. Other monomers besides acrylic acid can be used to form these polymers including such monomers as ethylene and propylene which act as diluents, and maleic anhydride which acts as a source of additional carboxylic groups.

In the thickener constituent, preferred for use are gum based thickeners, e.g., exopolysaccharides (also known as biopolymers) such as welan gum, xanthan gum, rhamsan gum, gellan gum, dextran gum, pullulan gum, curdlan gum; marine gums such as agar, seagel, carrageenan; plant exudates, such as locust bean gum, gum arabic, gum Karaya, tragacanth, Ghatti; seed gums such as guar gum, locust bean gum, okra, psyllium, mesquite; related derivatized compounds, e.g., gelatins, pectins, agars, carrageenans, locust beans, guars, xanthans, gellans and konjac gums. Of these are preferred gum based thickener based on exudates, such as locust bean gum, gum arabic, gum Karaya, tragacanth, Ghatti, and especially preferably based on gum Arabic (a.k.a. acacia gum).

The thickener constituent may be present in any effective amount such that it provides a desired increase in the viscosity of the flowable (e.g., melt) of the film forming composition while it is being manufactured. Advantageously the thickener constituent is present in amounts of up to about 25% wt., preferably in an amount of at least about 0.1% wt., to at least about 35% wt. Alternately the fragrance constituent forms at least 0.5% wt. of the fragranced film, and not in excess of about (in % wt.) 34%, 33%, 32%, 31%, 30%, 29%, 28%, 27%, 26%, 25%, 24%, 23%, 22%, 21%, 20%, 19%, 18%, 17%, 16%, 15% 14%, 13%, 12%, 11%, 10%, 9%, 8%, 7%, 6%, and 5% wt. Especially preferably the thickener constituent is present in amounts of from about 1% wt. to about 25% wt., and most preferably is present in an amount of from about 5% wt. to about 20% wt. based on the total weight of the fragranced film of which it forms a part.

The fragranced films optionally but particularly preferably include an organic solvent constituent. Mixtures of several organic solvents can also be used in the organic solvent constituent. Non-limiting examples of useful organic solvents include those which are at least partially water-miscible such as alcohols (e.g., ethanol, methanol, propanol, butanol), water-miscible ethers (e.g. diethylene glycol diethylether, diethylene glycol dimethylether, propylent glycol dimethylether), water-miscible glycol ether (e.g. propylene glycol monomethylether, propylene glycol mono ethylether, propylene glycol monopropylether, propylene glycol monobutylether, ethylene glycol monobutylether, dipropylene glycol monomethylether, dipropylene glycol monopropyl ether, dipropylene glycol monobutyl ether, diethyleneglycol monobutylether), lower esters of monoalkylethers of ethyleneglycol or propylene glycol (e.g. propylene glycol monomethyl ether acetate), as well as glycerine and trimethylol propane. The organic solvent constituent may function as a plasticizer in the fragranced film compositions. Particularly preferred for use in the organic solvent constituent are $C_2$-$C_8$ based polyalkylene glycols, and preferably one or more of polyethylene glycol, polypropylene glycol, a/o polybutylene glycol. When present, the organic solvent constituent forms up to about 20% wt., and is preferably present an amount of at least about 0.1% wt. Alternately the organic solvent constituent forms at least 0.5% wt. of the fragranced film, and not in excess of about (in % wt.) 20%, 19%, 18%, 17%, 16%, 15% 14%, 13%, 12%, 11%, 10%, 9%, 8%, 7%, 6%, and 5% wt. Especially preferably the organic solvent constituent is present in amounts of from about 1% wt. to about 10% wt., and but preferably is present in an amount of from about 2% wt. to about 7% wt. based on the total weight of the fragranced film of which it forms a part.

The fragranced films optionally but particularly preferably also comprise a carrier substance, which is preferably a micronized material. Nonlimiting examples of useful carrier substances include, crystalline polysaccharide polymers especially those selected from cellulose, alkyl celluloses, alkoxy celluloses, hydroxy alkyl celluloses, alkyl hydroxy alkyl celluloses, carboxy alkyl celluloses, carboxy alkyl hydroxy alkyl celluloses. Preferably the carrier substance is one or more microcrystalline polysaccharide polymers, especially one or more microcrystalline celluloses.

The carrier substance is preferably a free-flowing particulate material which comprises of particulates of polysaccharide polymers. Such may be of any useful particle size and/or particle size distribution, but smaller particle sizes are preferred.

Most preferably the carrier substance is a microcrystalline cellulose onto which the fragrance composition may be adsorbed or into which may be absorbed. Microcrystalline cellulose is a purified, partially depolymerized cellulose that is generally produced by treating a source of cellulose, preferably alpha cellulose in the form of a pulp from fibrous plants, with a mineral acid, preferably hydrochloric acid. The acid selectively attacks the less ordered regions of the cellulose polymer chain, thereby exposing and freeing the crystallite sites, forming the crystallite aggregates which constitute microcrystalline cellulose. These are then separated from the reaction mixture and washed to remove degraded by-products. The resulting wet mass, generally containing 40 to 60 wt % water, is referred to as hydrolyzed cellulose or more frequently, microcrystalline cellulose. Also useful is colloidal microcrystalline cellulose which may be obtained by reducing the particle size of microcrystalline cellulose and stabilizing the attrited particles to avoid formation of hard aggregates. The method of drying, i.e., removing the water from the wet cake, may be any method which ultimately produces a reconstitutable powder.

The carrier substance, and preferably when the carrier substance comprises microcrystalline cellulose, is provided to have an average particle size in the range of about 0.01 to about 1000 microns, preferably, have an average particle size in the range of about 0.01 to about 100 microns, preferably to about 50 microns. The carrier substance is also advantageously of a sufficiently small average particle size such that the resultant fragrancing film is translucent, preferably essentially transparent in appearance.

In the manufacture of the fragranced films, in certain embodiments it is preferred that the fragrance constituent is first adsorbed and/or absorbed onto the carrier substance prior to combining the fragrance compositions with the other constituents of the fragranced film.

Further, the adsorbed and/or absorbed fragrance composition, when added further constituents, is usually generally uniformly dispersed in the fluidified fragranced film composition before it is formed into a film, such as by casting, rolling, or other conventional process. Such uniform dispersion in the fluidified fragranced film composition also generally provides a relatively uniform distribution of the fragrance composition across all areas of the fragranced film ultimately formed therefrom.

In other embodiments, the fragrance not adsorbed and/or absorbed onto a carrier substance prior to combining the fragrance composition with other constituents of the fragranced film.

In addition to the foregoing recited constituents, the fragrance films may include one or more further optional constituents which may provide an aesthetic and/or technical benefit to the final fragranced films. Such include, without limitation: one or more surfactants (anionic, non-ionic, cationic, amphoteric), organic or inorganic fillers, colorants (e.g., dyes, pigments). Such may be added in any effective amount, and generally, the amount of each such further optional constituent typically does not exceed about 5% wt. of the total weight of the fragranced film composition of which it forms part. Alternately, the sum total of all of said further optional constituents which provide an aesthetic and/or technical benefit typically does not exceed about 20% wt. of the total weight of the fragranced film composition.

A preferred composition of a fragranced film is as follows:

| | |
|---|---|
| Polyvinyl alcohol | 40-70% wt. |
| Gum Arabic | 10-20% wt. |
| Propylene glycol | 0-10% wt. |
| Microcrystalline cellulose | 2-10% wt. |
| Fragrance composition | 10-45% wt. |
| Colorant (F&DC #1 Blue) | 0.06-0.1% wt. |

The fragranced film may have any suitable or desired dimension. Advantageously however, the fragranced film is at least to some degree flexible although, the fragranced film can form discrete monolithic articles such as pellets, spheroids or other regular or irregular geometric shapes. The fragranced film is most advantageously in the shape of a tape, ribbon, or sheet having a thickness in the range of about 5 microns-5000 microns, preferably, the range of about 10-1000 microns, and having a width and/or the length being at least 10 times, preferably at least 50 times that of the thickness dimension. In this manner, a sheet-like article may be formed. The sheet like article may be of any shape or configuration, need not necessarily be flat, but can be for example, a curl, spiral, or circular shaped article. Articles cut from a sheet having a particular ornamental shape, i.e. circle, square, star shape, may also be formed.

The fragranced film may be formed by any suitable method including casting techniques and extrusion techniques which are known to the art. In such a process the constituents may be combined to form a resin in which the polyvinyl alcohol polymer is fluidified, which can be achieved by adding the polyvinyl alcohol to a suitable solvent such as water, and organic solvent or a mixture of water within organic solvent, and/or optionally by heating the polyvinyl alcohol until it is rendered into a fluid state. Preferably, when a carrier substance is included, the fragrance composition is first adsorbed and/or absorbed prior to addition to the resin. Where a carrier substance is not included, the fragrance composition may be added directly to the resin. Thereafter further constituents can be blended it there with, and preferably blending ensures that the resultant fragranced film is essentially homogenous in the resin composition. Thereafter, the resin composition can be extruded, or cast form a fragranced film, such that the resultant fragranced film has a moisture content of preferably less than about 5% by weight, more preferably less than about 2.5% by weight, most preferably not more than about 1% by weight. Desirably the resultant fragranced film has sufficient mechanical strength such that it can be thereafter manually handled by an ultimate user of the fragranced film.

If desired, the fragranced film can be divided into pieces or articles. For example, in one embodiment the fragranced film is a sheet having an area of between about 10-30 square centimeters. In a further embodiment the fragranced film is a sheet having an area of between about 30-100 square centimeters. The dimensions of the sheets, pieces or articles are not critical, and may be forms to any desired shape. Advantageously however, the mass of the fragrance composition contained within each of the pieces or articles is sufficient such that a noticeable fragrancing benefit is provided when the pieces or article comprising the fragranced film is dispersed or dissolved in water.

The fragranced film of the present invention can be used in virtually any application wherein the amelioration of undesired malodors is a desired result. Such malodors may have any of a variety of sources, including (but not limited to) malodors associated with lavatories, malodors associated with food preparation and kitchen environments, malodors associated with refuse storage and disposal, malodors associated with vehicles, and the like. It is only necessary that the fragranced film be provided in the approximate locus of a malodors source in order to be considered useful and effective in its amelioration.

The fragranced films of the present invention can be used merely as fragranced films, or they may be incorporated into the construction of a further article. Nonlimiting examples of further articles include: sachets, pouches, cover films, sheets, containers which include as part of their construction, or alternately which contain the fragranced films, wrappings, coatings, and the like. Fragranced films of the invention can also be supplied as part of a multilayer, or a laminated construction or article, for example, the fragrance films may be supplied on a rigid carrier substrate, such as a coated paper, synthetic polymer film, metal foil, metallized polymer, or for that matter can be coded upon a particulate material or article which is at least partially coated with the fragranced films disclosed herein. The fragranced films of the present invention, can also be supplied onto flexible webs, textiles (woven or nonwoven) which operate as carrier substrates for the fragranced films. In such embodiments, the fragranced films, or the compositions forming the fragrance films, can be applied to such a flexible web, textile can be applied by padding, spring, soaking, rolling, and such an application a continuous film is not necessarily needed to be formed; rather, it is only required that the constituents of the fragranced film composition be applied to the webs, textiles. Of course, in such an application is preferred that a continuous fragranced film is applied to such carrier substrates, although such is not essential. In a certain preferred embodiment, a pouch, sachet, or article which further comprises one or more cleaning compositions and/or textile treatment compositions (i.e, surfactants, solvents, fabric softeners) include in their construction a fragranced film. An such an embodiment a consumer utilizing in the pouch, sachet, or article, cleaning composition and/or textile treatment composition concurrently with the fragrance film to an appliance. Such appliances include laundry appliances, i.e., washing machines, dryers, and the like Such appliances also include dishwashers which are advantageously treated utilizing the fragranced film. Dishwashers are frequently sources of malodors, which typically emanate from the residual water containing food wastes which may be present in the base or sump and, which are not completely flushed out at the conclusion of a wash/rinse cycle but are retained within the dishwasher prior to the next washing operation. Such malodors can be particularly noxious, as it is to be considered is that between washing cycles, such residual water is maintained in a generally moist, dark and sealed environment until a consumer opens the dishwasher door, which releases the malodors.

Articles which are formed and/or which incorporate into their construction the fragranced films taught herein also provide the benefit of a desired fragrancing effect prior to the use of any such articles. Frequently, shelf storage of many household cleaning products allows for the buildup of malodors within the packaging containing such household cleaning products, and prior to their use. When a consumer desires to use such an article which is to be withdrawn from the packaging in which it is supplied, opening of the packaging frequently also releases malodorous compounds city ambient environment. Utilization of the fragrancing films in the articles which are withdrawn from the packaging, or for that matter, use of the fragrancing films in forming part of the packaging, may advantageously ameliorate the perception of such undesired malodors.

In a preferred embodiment, fragranced films, articles formed from the fragranced film or which contain the fragranced film, are provided to a lavatory appliance. In one aspect, a piece of the fragranced film was applied to a sidewall, preferably an interior sidewall or other part of a lavatory appliance such that the fragranced film adheres to the lavatory appliance. Advantageously, such is a surface of a urinal, toilet bowl, or bidet at which surface the fragranced film has or will come and contact with water. In another aspect, the fragrance film is applied directly to water already present within a lavatory appliance, such as to the surface of the water at the base of a toilet bowl which is usually present between flushes. When contacted with water, the fragranced film advantageously generally rapidly disperses or is dissolved in the water, and this releases a perceptible fragrancing effect.

In another preferred embodiment, fragranced films, articles formed from the fragranced film or which contain the fragranced film, are provided to a kitchen appliance, as has been described above. Such kitchen environments may be of the type typically encountered in private homes, or private residences, as well as in larger kitchens such as institutional, commercial as well as restaurant environments.

In a still further preferred embodiment, fragranced films, articles formed from the fragranced film or which contain the fragranced film, are provided to a laundry appliance, e.g, a washing machine, dryer, as has been described above. Such laundry appliances may be of the type typically encountered in private homes a private residences, but may also be used in larger such appliances, such as are typically encountered in institutional, commercial as well as restaurant environments.

In another preferred embodiment, fragranced films, articles formed from the fragranced film or which contain the fragranced film, are utilized in storage and/or transport containers utilized in the disposal of waste products, e.g, trash bins, garbage cans, dumpsters, and the like. Such storage and/or transport containers may be of the type typically encountered in private homes a private residences, but may also be used in larger such appliances, such as are typically encountered in institutional, commercial as well as restaurant environments.

In another preferred embodiment, fragranced films, articles formed from the fragranced film or which contain the fragranced film, are provided to vehicle in order to ameliorate malodors which may be encountered to therein. Without limitation, such include automobiles, trucks, trailers, airplanes, watercraft (i.e. boats), and the like.

In a still further preferred embodiment, fragranced films, articles formed from the fragranced film or which contain the fragranced films disclosed herein may be used in the air treatment, more particularly in the amelioration of malodors in a locus, such as a room, cabin or other environment, e.g, the interior of a storage container, luggage, and the like.

Articles formed from the fragranced film may be supplied in dispensers which contain one or more discrete pieces of the fragrance film and/or articles which include the fragrance film. For example, a container which is used to store a plurality of individual articles may be provided, and such a container may be placed in the near proximity of a lavatory appliance. Such container provides a convenient method for retaining, and when necessary providing to a person a fragranced film which can be applied to a lavatory appliance in any of the manners described above, when desired or when necessary. As a further example is provided a dispenser which has a restricted opening or restricted openings, whereby a quantity of fragranced film is contained within the interior, preferably wherein the fragrance film is in the form of its relatively small particles such that, when desired or necessary, one or more of such small particles can be dispensed such as by strewing from the dispenser via the one or more restricted openings. Other containers and dispensers are also feasible.

The fragrance films of the present invention provide a highly effective means to ameliorate the undesired effects of malodors, particularly as encountered in household environments, in vehicles, as well as in commercial/institutional environments.

Nonlimiting examples of fragranced films, including certain preferred embodiments thereof, as well as several "comparative" examples are disclosed hereinafter.

EXAMPLES

As previously stated, particularly preferred fast dissolving water soluble films of the invention are those in which the fragrance constituent concurrently satisfy the following (averaged) parameters: (a) a c Log P<3.00; (b) a Vapor Pressure >0.1 mm Hg; (c) a molecular weight of <180. Such a requirement are met by the following "example" compositions which are identified by a digit prepended by the letter "E". Such a requirement are not met by the following "comparative" compositions which are identified by a digit prepended by the letter "C".

The fast dissolving films used in the example and comparative example compositions were formed by the same method, and apart from the fragrance composition included, were formed from the same amounts of the same materials. Thus apart from the specific fragrance composition, all films formed were produced in the same manner and yielded films of identical thickness and other physical characteristics. The composition of the films are as follows:

|  | % wt. |
| --- | --- |
| polyvinyl alcohol | 57.9 |
| gum Arabic | 10.0 |
| propylene glycol | 5.0 |
| microcrystalline cellulose | 2.0 |
| colorant | 0.1 |
| fragrance composition | 25.0 |

Thus, the only variant in the films used was the specific fragrance constituent present, and if the components present therein met the parameters (a), (b) and (c) disclosed previously.

A first "example" composition of a fast dissolving fragranced film of the invention is as follows:

(Example) E1

"Formula Fruity Floral"

| Raw Name (code) | % | cLogP | MW (g/mol) | Vapor Pressure (mm Hg) | <3 cLogP and >0.1 VP and <180 MW |
| --- | --- | --- | --- | --- | --- |
| Raw Material 53 | 2.35 | −0.64 | 134.18 | 0.0319 | |
| Raw Material 71 | 0.80 | 1.82 | 102.18 | 0.5870 | 0.80 |
| Raw Material 114 | 0.50 | 1.86 | 128.17 | 3.0100 | 0.50 |
| Raw Material 113 | 1.00 | 1.93 | 166.22 | 0.0875 | |
| Raw Material 26 | 5.20 | 2.08 | 150.18 | 0.1250 | 5.20 |
| Raw Material 76 | 4.50 | 2.11 | 172.27 | 0.0034 | |
| Raw Material 60 | 2.00 | 2.26 | 130.19 | 5.9000 | 2.00 |
| Raw Material 117 | 1.10 | 2.34 | 164.20 | 0.0733 | |
| Raw Material 106 | 0.00 | 2.35 | 160.81 | 0.1510 | 0.00 |
| Raw Material 70 | 7.20 | 2.51 | 192.21 | 0.0004 | |
| Raw Material 47 | 0.20 | 2.72 | 198.62 | 0.0132 | |
| Raw Material 127 | 0.90 | 2.85 | 138.21 | 0.2380 | 0.90 |
| Raw Material 85 | 1.50 | 3.04 | 140.23 | 0.5240 | |
| Raw Material 12 | 0.50 | 3.05 | 186.25 | 0.0977 | |
| Raw Material 100 | 0.01 | 3.08 | 142.24 | 0.0090 | |
| Raw Material 94 | 0.10 | 3.10 | 168.24 | 0.0443 | |
| Raw Material 96 | 0.30 | 3.22 | 196.20 | 0.0000 | |
| Raw Material 81 | 1.00 | 3.38 | 154.25 | 0.0521 | |
| Raw Material 86 | 0.40 | 3.38 | 156.27 | 0.0041 | |
| Raw Material 39 | 3.34 | 3.45 | 152.24 | 0.0596 | |
| Raw Material 50 | 8.10 | 3.47 | 156.27 | 0.0788 | |
| Raw Material 112 | 0.10 | 3.48 | 192.26 | 0.0172 | |
| Raw Material 122 | 0.01 | 3.52 | 150.22 | 0.0094 | |
| Raw Material 31 | 2.00 | 3.55 | 196.29 | 0.0638 | |
| Raw Material 41 | 1.56 | 3.55 | 151.25 | 0.0429 | |
| Raw Material 115 | 0.01 | 3.58 | 154.25 | 0.4560 | |
| Raw Material 8 | 0.60 | 3.60 | 184.28 | 0.0025 | |
| Raw Material 66 | 0.80 | 3.91 | 190.29 | 0.0048 | |
| Raw Material 65 | 5.50 | 3.94 | 190.29 | 0.0028 | |
| Raw Material 129 | 3.39 | 3.96 | 198.31 | 0.0312 | |
| Raw Material 82 | 1.00 | 4.02 | 196.29 | 0.0864 | |
| Raw Material 35 | 0.02 | 4.09 | 185.70 | 0.0043 | |
| Raw Material 49 | 0.05 | 4.16 | 192.30 | 0.0157 | |
| Raw Material 121 | 2.00 | 4.34 | 196.29 | 0.0319 | |
| Raw Material 83 | 5.00 | 4.36 | 204.31 | 0.0020 | |

-continued

"Formula Fruity Floral"

| Raw Name (code) | % | cLogP | MW (g/mol) | Vapor Pressure (mm Hg) | <3 cLogP and >0.1 VP and <180 MW |
| --- | --- | --- | --- | --- | --- |
| Raw Material 128 | 0.90 | 4.37 | 184.28 | 0.0043 | |
| Raw Material 7 | 0.50 | 4.67 | 184.32 | 1.0500 | |
| Raw Material 125 | 0.04 | 4.76 | 182.07 | 0.0111 | |
| Raw Material 103 | 6.28 | 4.83 | 136.24 | 1.0300 | |
| Raw Material 119 | 7.00 | 4.88 | 136.24 | 0.7020 | |
| Raw Material 74 | 10.70 | 4.89 | 216.33 | 0.0003 | |
| Raw Material 1 | 0.54 | 5.16 | 184.32 | 0.0088 | |
| Raw Material 78 | 4.50 | 5.18 | 234.38 | 0.0026 | |
| Raw Material 23 | 0.40 | mixture | mixture | #N/A | |
| Raw Material 42 | 0.40 | NAT | NAT | 0.1000 | |
| Raw Material 79 | 5.70 | NAT | NAT | 0.2 | |
| | | | | | 9.40% wt |

(Example) E2

"Formula Ocean"

| Raw Name (code) | % | cLogP | MW (g/mol) | Vapor Pressure (mm Hg) | <3 cLogP and >0.1 VP and <180 MW |
| --- | --- | --- | --- | --- | --- |
| Raw Material 43 | 2.13 | 1.51 | 146.15 | 0.0003 | |
| Raw Material 26 | 3.00 | 2.08 | 150.18 | 0.1250 | 3.00 |
| Raw Material 36 | 0.38 | 2.43 | 178.87 | 0.0004 | |
| Raw Material 64 | 0.25 | 2.54 | 206.24 | 0.0008 | |
| Raw Material 118 | 0.63 | 2.60 | 154.25 | 0.0108 | |
| Raw Material 44 | 0.25 | 2.62 | 122.17 | 0.8390 | 0.25 |
| Raw Material 30 | 1.25 | 2.71 | 154.25 | 0.0002 | |
| Raw Material 63 | 0.25 | 2.73 | 164.20 | 0.0057 | |
| Raw Material 87 | 0.75 | 2.87 | 154.25 | 0.2530 | 0.75 |
| Raw Material 45 | 12.50 | 2.98 | 192.26 | 0.0083 | |
| Raw Material 37 | 0.88 | 3.04 | 152.24 | 0.0060 | |
| Raw Material 81 | 2.13 | 3.38 | 154.25 | 0.0521 | |
| Raw Material 86 | 0.25 | 3.38 | 156.27 | 0.0041 | |
| Raw Material 39 | 11.50 | 3.45 | 152.24 | 0.0596 | |
| Raw Material 50 | 8.75 | 3.47 | 156.27 | 0.0788 | |
| Raw Material 31 | 11.88 | 3.55 | 196.29 | 0.0638 | |
| Raw Material 41 | 5.63 | 3.55 | 151.25 | 0.0429 | |
| Raw Material 115 | 1.00 | 3.58 | 154.25 | 0.4560 | |
| Raw Material 14 | 1.88 | 4.02 | 196.29 | 0.0137 | |
| Raw Material 52 | 3.38 | 4.05 | 170.21 | 0.0097 | |
| Raw Material 68 | 3.00 | 4.10 | 196.29 | 0.0297 | |
| Raw Material 22 | 0.50 | 4.16 | 192.30 | 0.0129 | |
| Raw Material 5 | 0.63 | 4.25 | 170.30 | 0.0393 | |
| Raw Material 38 | 0.25 | 4.33 | #REF! | 0.0001 | |
| Raw Material 121 | 2.00 | 4.34 | 196.29 | 0.0319 | |
| Raw Material 80 | 7.88 | 4.36 | 204.31 | 0.0020 | |
| Raw Material 128 | 0.63 | 4.37 | 184.28 | 0.0043 | |
| Raw Material 89 | 0.56 | 4.39 | 198.06 | 0.0596 | |
| Raw Material 21 | 7.13 | 4.57 | 208.26 | 0.0024 | |
| Raw Material 51 | 0.06 | 4.65 | 200.32 | 0.0634 | |
| Raw Material 7 | 1.38 | 4.67 | 184.32 | 1.0500 | |
| Raw Material 73 | 0.38 | 4.84 | 220.27 | 0.0000 | |
| Raw Material 48 | 1.50 | 4.87 | 220.27 | 0.0000 | |
| Raw Material 18 | 0.13 | 5.41 | 236.40 | 0.0022 | |
| Raw Material 123 | 0.38 | 5.80 | 226.40 | 0.0010 | |
| Raw Material 62 | 3.13 | NAT | NAT | 1.7000 | |
| Raw Material 104 | 1.25 | NAT | NAT | 0.9000 | |
| Raw Material 108 | 0.63 | NAT | NAT | 0.0100 | |
| 100% wt. | | | | | 4.00% wt |

(Example) E3

"Formula Woody Floral"

| Raw Name (code) | % | cLogP | MW (g/mol) | Vapor Pressure (mm Hg) | <3 cLogP and >0.1 VP and <180 MW |
|---|---|---|---|---|---|
| Raw Material 53 | 1.64 | −0.64 | 134.18 | 0.0319 | |
| Raw Material 70 | 3.00 | 2.51 | 192.21 | 0.0004 | |
| Raw Material 116 | 1.00 | 2.63 | 194.27 | 0.0025 | |
| Raw Material 84 | 0.50 | 2.76 | 144.21 | 2.0600 | 0.50 |
| Raw Material 99 | 0.00 | 2.84 | 138.21 | 0.1560 | 0.00 |
| Raw Material 127 | 1.00 | 2.85 | 138.21 | 0.2380 | 0.30 |
| Raw Material 130 | 0.30 | 2.85 | 138.10 | 0.2380 | 1.00 |
| Raw Material 11 | 0.10 | 3.03 | 128.22 | 1.0500 | |
| Raw Material 85 | 1.00 | 3.04 | 140.23 | 0.5240 | |
| Raw Material 12 | 1.00 | 3.05 | 186.25 | 0.0977 | |
| Raw Material 101 | 0.00 | 3.06 | 140.26 | 0.2140 | |
| Raw Material 100 | 0.00 | 3.08 | 142.24 | 0.0090 | |
| Raw Material 94 | 0.05 | 3.10 | 168.24 | 0.0443 | |
| Raw Material 96 | 0.50 | 3.22 | 196.20 | 0.0000 | |
| Raw Material 131 | 1.00 | 3.25 | 158.20 | 0.0015 | |
| Raw Material 39 | 1.00 | 3.45 | 152.24 | 0.0596 | |
| Raw Material 50 | 10.00 | 3.47 | 156.27 | 0.0788 | |
| Raw Material 46 | 1.00 | 3.72 | 190.29 | 15.4000 | |
| Raw Material 65 | 2.00 | 3.94 | 190.29 | 0.0028 | |
| Raw Material 3 | 0.10 | 4.09 | 156.27 | 0.1580 | |
| Raw Material 97 | 1.50 | 4.22 | 256.35 | 0.0000 | |
| Raw Material 83 | 20.00 | 4.36 | 204.31 | 0.0020 | |
| Raw Material 128 | 1.25 | 4.37 | 184.28 | 0.0043 | |
| Raw Material 4 | 0.05 | 4.53 | 168.28 | 0.0423 | |
| Raw Material 7 | 0.15 | 4.67 | 184.32 | 1.0500 | |
| Raw Material 93 | 2.50 | 4.78 | 206.33 | 0.0037 | |
| Raw Material 69 | 15.00 | 4.88 | 238.37 | 0.0000 | |
| Raw Material 119 | 1.00 | 4.88 | 136.24 | 0.7020 | |
| Raw Material 74 | 10.00 | 4.89 | 216.33 | 0.0003 | |
| Raw Material 98 | 0.50 | 5.05 | 220.56 | 0.0005 | |
| Raw Material 75 | 10.00 | 5.06 | 222.28 | 0.0000 | |
| Raw Material 6 | 0.05 | 5.16 | 184.32 | 0.0088 | |
| Raw Material 78 | 7.50 | 5.18 | 234.38 | 0.0026 | |
| Raw Material 2 | 0.20 | 5.30 | 210.36 | 0.0040 | |
| Raw Material 28 | 0.30 | 5.71 | 242.40 | 0.0014 | |
| Raw Material 16 | 0.30 | | | | |
| Raw Material 102 | 4.50 | | | 1.2000 | |
| | 100% wt. | | | | 1.80% wt. |

(Example) E4

"Formula Floral BQT"

| Raw Name (code) | % | cLogP | MW (g/mol) | Vapor Pressure (mm Hg) | <3 cLogP and >0.1 VP and <180 MW |
|---|---|---|---|---|---|
| Raw Material 53 | 0.86 | −0.64 | 134.18 | 0.0319 | |
| Raw Material 67 | 0.09 | 0.82 | 128.13 | 0.0003 | |
| Raw Material 43 | 0.80 | 1.51 | 146.15 | 0.0003 | |
| Raw Material 59 | 1.20 | 1.55 | 166.18 | 0.0002 | |
| Raw Material 24 | 5.00 | 1.76 | 136.15 | 0.0192 | |
| Raw Material 91 | 0.01 | 1.83 | 136.15 | 0.2570 | 0.01 |
| Raw Material 10 | 1.50 | 2.08 | 156.23 | 0.0073 | |
| Raw Material 32 | 1.50 | 2.30 | 222.24 | 0.0001 | |
| Raw Material 92 | 0.50 | 2.41 | 146.19 | 0.0158 | |
| Raw Material 63 | 0.05 | 2.73 | 164.20 | 0.0057 | |
| Raw Material 84 | 0.50 | 2.76 | 144.21 | 2.0600 | 0.50 |
| Raw Material 127 | 0.20 | 2.85 | 138.21 | 0.2380 | 0.20 |
| Raw Material 85 | 0.10 | 3.04 | 140.23 | 0.5240 | |
| Raw Material 131 | 1.05 | 3.25 | 158.20 | 0.0015 | |
| Raw Material 8 | 4.00 | 3.60 | 184.28 | 0.0025 | |
| Raw Material 65 | 1.50 | 3.94 | 190.29 | 0.0028 | |

"Formula Floral BQT"

| Raw Name (code) | % | cLogP | MW (g/mol) | Vapor Pressure (mm Hg) | <3 cLogP and >0.1 VP and <180 MW |
|---|---|---|---|---|---|
| Raw Material 3 | 0.20 | 4.09 | 156.27 | 0.1580 | |
| Raw Material 83 | 15.60 | 4.36 | 204.31 | 0.0020 | |
| Raw Material 128 | 1.20 | 4.37 | 184.28 | 0.0043 | |
| Raw Material 25 | 1.00 | 4.45 | 208.35 | 0.0000 | |
| Raw Material 4 | 0.05 | 4.53 | 168.28 | 0.0423 | |
| Raw Material 7 | 0.10 | 4.67 | 184.32 | 1.0500 | |
| Raw Material 93 | 2.65 | 4.78 | 206.33 | 0.0037 | |
| Raw Material 103 | 5.00 | 4.83 | 136.24 | 1.0300 | |
| Raw Material 69 | 13.50 | 4.88 | 238.37 | 0.0000 | |
| Raw Material 74 | 10.00 | 4.89 | 216.33 | 0.0003 | |
| Raw Material 75 | 10.20 | 5.06 | 222.28 | 0.0000 | |
| Raw Material 6 | 0.05 | 5.16 | 184.32 | 0.0088 | |
| Raw Material 78 | 20.50 | 5.18 | 234.38 | 0.0026 | |
| Raw Material 16 | 0.10 | | | | |
| Raw Material 109 | 1.00 | #N/A | #N/A | #N/A | |
| | 100% wt. | | | | 0.71% wt. |

(Comparative) C1

"Formula Floral Green"

| Raw Name (code) | % | cLogP | MW (g/mol) | Vapour Pressure (mm Hg) | <3 cLogP and >0.1 VP and <180 MW |
|---|---|---|---|---|---|
| Raw Material 53 | 7.60 | −0.64 | 134.18 | 0.0319 | |
| Raw Material 58 | 0.03 | 0.30 | 140.14 | 0.0001 | |
| Raw Material 27 | 0.50 | 1.08 | 108.14 | 0.0331 | |
| Raw Material 43 | 0.53 | 1.51 | 146.15 | 0.0003 | |
| Raw Material 111 | 3.18 | 1.57 | 122.17 | 0.0147 | |
| Raw Material 91 | 0.04 | 1.83 | 136.15 | 0.2570 | 0.04 |
| Raw Material 113 | 0.05 | 1.93 | 166.22 | 0.0875 | |
| Raw Material 90 | 0.32 | 2.04 | 178.23 | 0.0076 | |
| Raw Material 26 | 9.09 | 2.08 | 150.18 | 0.1250 | 9.09 |
| Raw Material 76 | 11.73 | 2.11 | 172.27 | 0.0034 | |
| Raw Material 117 | 0.18 | 2.34 | 164.20 | 0.0733 | |
| Raw Material 70 | 2.18 | 2.51 | 192.21 | 0.0004 | |
| Raw Material 72 | 0.09 | 2.61 | 142.20 | 0.7960 | 0.09 |
| Raw Material 63 | 0.53 | 2.73 | 164.20 | 0.0057 | |
| Raw Material 99 | 0.02 | 2.84 | 138.21 | 0.1560 | 0.02 |
| Raw Material 29 | 0.91 | 2.85 | 154.25 | 0.0002 | |
| Raw Material 127 | 0.60 | 2.85 | 138.21 | 0.2380 | 0.60 |
| Raw Material 88 | 0.64 | 2.87 | 154.25 | 0.2530 | 0.64 |
| Raw Material 45 | 3.09 | 2.98 | 192.26 | 0.0083 | |
| Raw Material 37 | 0.45 | 3.04 | 152.24 | 0.0060 | |
| Raw Material 85 | 1.71 | 3.04 | 140.23 | 0.5240 | |
| Raw Material 12 | 1.09 | 3.05 | 186.25 | 0.0977 | |
| Raw Material 126 | 0.47 | 3.09 | 142.24 | 0.9490 | |
| Raw Material 61 | 1.78 | 3.13 | 154.25 | 1.1100 | |
| Raw Material 13 | 0.18 | 3.18 | 156.23 | 0.4970 | |
| Raw Material 96 | 0.39 | 3.22 | 196.20 | 0.0000 | |
| Raw Material 131 | 0.45 | 3.25 | 158.20 | 0.0015 | |
| Raw Material 50 | 8.00 | 3.47 | 156.27 | 0.0788 | |
| Raw Material 31 | 5.73 | 3.55 | 196.29 | 0.0638 | |
| Raw Material 41 | 1.32 | 3.55 | 151.25 | 0.0429 | |
| Raw Material 124 | 0.01 | 3.55 | 154.53 | 0.0779 | |
| Raw Material 115 | 0.27 | 3.58 | 154.25 | 0.4560 | |
| Raw Material 15 | 0.32 | 3.67 | 170.25 | 0.1520 | |
| Raw Material 65 | 1.86 | 3.94 | 190.29 | 0.0028 | |
| Raw Material 52 | 0.18 | 4.05 | 170.21 | 0.0097 | |
| Raw Material 3 | 0.59 | 4.09 | 156.27 | 0.1580 | |
| Raw Material 80 | 23.11 | 4.36 | 204.31 | 0.0020 | |
| Raw Material 128 | 0.91 | 4.37 | 184.28 | 0.0043 | |
| Raw Material 54 | 0.32 | 4.45 | 192.02 | 0.0108 | |
| Raw Material 7 | 0.55 | 4.67 | 184.32 | 1.0500 | |
| Raw Material 95 | 1.05 | 4.78 | 206.33 | 0.0200 | |

-continued

"Formula Floral Green"

| Raw Name (code) | % | cLogP | MW (g/mol) | Vapour Pressure (mm Hg) | <3 cLogP and >0.1 VP and <180 MW |
|---|---|---|---|---|---|
| Raw Material 120 | 6.36 | 4.88 | 136.24 | 0.7020 | |
| Raw Material 6 | 0.95 | 5.16 | 184.32 | 0.0088 | |
| Raw Material 17 | 0.05 | 5.18 | 236.40 | 0.0022 | |
| Raw Material 2 | 0.38 | 5.30 | 210.36 | 0.0040 | |
| Raw Material 23 | 0.21 | Mixture | Mixture | #N/A | |
| | 100% wt. | | | | 10.48% wt |

(Comparative) C2

"Formula Fruity Melon"

| Raw Material (code) | % | cLogP | MW (g/mol) | Vapour Pressure (mm Hg) | <3 cLogP and >0.1 VP and <180 MW |
|---|---|---|---|---|---|
| Raw Material 53 | 44.18 | −0.64 | 134.18 | 0.0319 | |
| Raw Material 58 | 3.17 | 0.30 | 140.14 | 0.0001 | |
| Raw Material 55 | 7.33 | 0.72 | 130.14 | 0.6450 | 7.33 |
| Raw Material 33 | 2.67 | 1.77 | 116.16 | 13.7000 | 2.67 |
| Raw Material 56 | 6.00 | 1.85 | 116.16 | 10.9000 | 6.00 |
| Raw Material 19 | 5.67 | 2.12 | 130.19 | 5.0000 | 5.67 |
| Raw Material 60 | 7.33 | 2.26 | 130.19 | 5.9000 | 7.33 |
| Raw Material 117 | 0.83 | 2.34 | 164.20 | 0.0733 | |
| Raw Material 99 | 0.13 | 2.84 | 138.21 | 0.1560 | 0.13 |
| Raw Material 107 | 1.33 | 2.94 | 184.28 | 0.0551 | |
| Raw Material 85 | 7.33 | 3.04 | 140.23 | 0.5240 | |
| Raw Material 101 | 0.02 | 3.06 | 140.26 | 0.2140 | |
| Raw Material 9 | 2.67 | 3.10 | 206.24 | 0.0017 | |
| Raw Material 20 | 5.67 | 3.25 | 158.24 | 0.7050 | |
| Raw Material 8 | 1.67 | 3.60 | 184.28 | 0.0025 | |
| Raw Material 46 | 2.33 | 3.72 | 190.29 | 15.4000 | |
| Raw Material 65 | 1.67 | 3.94 | 190.29 | 0.0028 | |
| | 100% wt. | | | | 29.13% wt. |

(Comparative) C3

"Formula Fruity Blueberry"

| Raw Material (code) | % | cLogP | MW (g/mol) | Vapour Pressure (mm Hg) | <3 cLogP and >0.1 VP and <180 MW |
|---|---|---|---|---|---|
| Raw Material 53 | 58.50 | −0.64 | 134.18 | 0.0319 | |
| Raw Material 58 | 0.88 | 0.30 | 140.14 | 0.0001 | |
| Raw Material 105 | 13.27 | 1.48 | 164.20 | 0.0004 | |
| Raw Material 56 | 0.44 | 1.85 | 116.16 | 10.9000 | 0.44 |
| Raw Material 90 | 4.42 | 2.04 | 178.23 | 0.0076 | |
| Raw Material 26 | 14.16 | 2.08 | 150.18 | 0.1250 | 14.16 |
| Raw Material 57 | 0.44 | 2.26 | 130.19 | 5.8600 | 0.44 |
| Raw Material 34 | 0.18 | 2.79 | 216.28 | 0.0422 | |
| Raw Material 110 | 2.21 | 3.01 | 208.26 | 0.0029 | |
| Raw Material 9 | 1.77 | 3.10 | 206.24 | 0.0017 | |
| Raw Material 8 | 2.65 | 3.60 | 184.28 | 0.0025 | |
| Raw Material 49 | 0.18 | 4.16 | 192.30 | 0.0157 | |
| Raw Material 77 | 0.88 | 4.42 | 192.30 | 0.0144 | |
| | 100% wt. | | | | 15.04% wt. |

Films formed from the foregoing example compositions and example compositions were tested in accordance with the following general protocols:

A. Fragrance Delivery to a Headspace from Dissolved Film in Water

This test evaluated the relative odor intensity of fragrance delivered from a sample of a PVOH film dissolved in water. For the test were used: (a) samples of PVOH films according to E1, E2, E3, E4, C1, C2 and C3; (b) water at room temperature (20° C.), 3 gallon (approx. 12 liter) containers for containing the water, and (d) odor testing booths, having a volume of 104 cubic feet (2.94 cubic meters).

First, the odor testing booths were purged, equilibrated and placed on test mode. A container was placed in each of the odor testing booths and filled with approx. 6 liters of room temperature water. Thereafter, a 2 inch by 2 inch (5.08 cm by 5.08 cm) sample of PVOH films according to E1, E2, E3, E4, C1, C2 and C3, each weighing 0.15 grams, were individually delivered to different buckets in different odor testing booths; each sample was observed to dissolve in the water of each container in not more than 55 seconds. Subsequently the containers with dissolved PVOH film samples were allowed to equilibrate for 15 minutes. Thereafter members (comprising 30 persons) of a trained panel evaluated the perceived bloom intensity of the fragrance in each odor testing booth and reported their results, on a 10 point scale where a value of "0" was indicative of no perceived fragrance, to a maximum value of "10" which was indicative of a "very strong" fragrance perception. The results were averaged, and are reported (at a 95% confidence level) for each of the PVOH films according to E1, E2, E3, E4, C1, C2 and C3 on the following Table 1.

TABLE 1

| | Sample | | | | | | |
|---|---|---|---|---|---|---|---|
| | E1 | E2 | E3 | E4 | C1 | C2 | C3 |
| (avg.) score, fragrance intensity | 4.8 | 6.0 | 6.3 | 6.8 | 3.3 | 1.2 | 1.6 |

As can be seen from the foregoing results of Table 1, PVOH films according to the invention exhibited far superior fragrance delivery to the headspace of each of the odor testing booths, even following a 15 minute residence time. The compositions disclosed on Table 1 demonstrate the utility of the PVOH films of the invention in surface treatment applications, i.e., hard surface treatment compositions.

B. Fragrance Delivery/Malodour Control from Dissolved Film to an Automatic Dishwasher This test evaluated the relative odor intensity delivered from samples of a PVOH film and their efficacy in providing a fragrance benefit and in controlling malodours in an automatic dishwasher. For the test were used: (a) samples of PVOH films according to E1, E2, E3, E4, C1, C2 and C3 each weighing 0.15 grams and having a dimension of 2 inch by 2 inch (5.08 cm by 5.08 cm); (b) standardized food soils prepared according to the CAM-202E protocol from the IKW method which included both a meat mixture and a fat mixture; and, (c) automatic dishwashers.

According to the test protocol, first food soil malodor was prepared using CAM-202E protocol. Next, automatic dishwashers were cleaned with unscented detergent prior to use. Then, samples of the food soil malodor was placed at the bottom of each automatic dishwasher (35 g of meat mixture and 50 g of fat mixture), and immediately thereafter dishwasher doors were closed and dishwashers were allowed to equilibrate for three days. One such treated dishwasher was later used as a control and was not treated with any of the sample PVOH films according to E1, E2, E3, E4, C1, C2 and C3. On the third day, to the soiled but otherwise empty dishwashers was provided a sample of one of the PVOH films of E1, E2, E3, E4, C1, C2 and C3, and each dishwasher was operated at a "normal" wash cycle setting which provided a water temperature of (45-65° C.); PVOH films of the invention were observed to dissolved in not more than 15 seconds. After completing the "normal" wash cycle, members (comprising 30 persons) of a trained panel evaluated each of the dishwashers for (a) the residual malodor perceived, and (b) the fragrance intensity. For purposes of this evaluation the control dishwasher untreated with any PVOH film was assigned a ranking of "8" for malodor, and the relative perceptions of the panelists were established relative thereto. All rankings were on a 10 point scale where a value of "0" was indicative of no perceived fragrance, or no residual malodour perception, to a maximum value of "10" which was indicative of a "very strong" fragrance perception or residual malodour perception. The results were averaged, and are reported (at a 95% confidence level) for each of the PVOH films according to E1, E2, E3, E4, C1, C2 and C3 on the following Table 2.

TABLE 2

| | Sample | | | | | | | |
|---|---|---|---|---|---|---|---|---|
| | E1 | E2 | E3 | E4 | Control | C1 | C2 | C3 |
| (avg.) score, fragrance intensity | 3.9 | 4.2 | 4.5 | 4.8 | — | 2.9 | 1.2 | 1.8 |
| (avg.) score, residual malodour intensity | 4.2 | 2.8 | 2.8 | 2.1 | 8 | 5.5 | 8.5 | 7.6 |

C. Fragrance Delivery/Malodour Control from Dissolved Film to an Automatic Washing Machine This test evaluated the relative odor intensity delivered from samples of a PVOH film and their efficacy in providing a fragrance benefit and controlling musty/mildew malodours in an automatic laundry washing machine. For the test were used: (a) samples of PVOH films according to E1, E2, E3, E4, C1, C2 and C3 each weighing 0.15 grams and having a dimension of 2 inch by 2 inch (5.08 cm by 5.08 cm); (b) a standardized musty/mildew malodour composition (proprietary composition of the Applicant); and, (c) automatic laundry washing machines.

According to the test protocol, each of the automatic laundry washing machines were cleaned with unscented detergent prior to use. Next an aliquot (the same amount was used in each of the tests in each of the washing machines) of the standardized musty/mildew malodour material was placed in each of the washing machines. and immediately thereafter the lids of each of the washing machines was were closed and each of the washing machines were allowed to equilibrate for two days. One such treated washing machine was later used as a control and was not treated with any on of sample PVOH films according to E1, E2, E3, E4, C1, C2 and C3, but rather was only operated using an unscented laundry detergent it is served as a "control" and a reference for residual malodor. On the second day, to the washing machines was provided a sample of one of the PVOH films of E1, E2, E3, E4, C1, C2 and C3, and each of the washing machines was operated wash cycle setting which provided a warm wash (32° C.) and cold rinse (27° C.); PVOH films of the invention were observed to dissolved in not more than 45 seconds. After completing the washing cycle, members (comprising 30 persons) of a trained panel evaluated each of the washing machines for (a) the residual malodor perceived, and (b) the fragrance intensity. For purposes of this evaluation the control washing machine which was operated, but which was untreated with any PVOH film was assigned a ranking of "8" for malodor, and the perceptions of the panelists for the other washing machines were established relative thereto. All rankings were on a 10 point scale where a value of "0" was indicative of no perceived fragrance, or no residual malodour perception, to a maximum value of "10" which was indicative of a "very strong" fragrance perception or residual malodour perception. The results were averaged, and are reported (at a 95% confidence level) for each of the PVOH films according to E1, E2, E3, E4, C1, C2 and C3 on the following Table 3.

TABLE 3

| | Sample | | | | | | | |
|---|---|---|---|---|---|---|---|---|
| | E1 | E2 | E3 | E4 | Control | C1 | C2 | C3 |
| (avg.) score, fragrance intensity | 4.0 | 5.3 | 4.9 | 6.1 | — | 2.9 | 2.5 | 2.8 |
| (avg.) score, residual malodour intensity | 4.3 | 3.5 | 3.7 | 3.7 | 8 | 5.4 | 8.6 | 7.3 |

D. Fragrance Delivery/Malodour Control from Dissolved Film to Lavatory Appliance (Toilet) This test evaluated the relative odor intensity delivered from samples of a PVOH film and their efficacy in providing a fragrance benefit and controlling malodours in an lavatory appliance, more specifically, a toilet bowl. For the test were used: (a) samples of PVOH films according to E1, E2, E3, E4, C1, C2 and C3; (b) standardized liquid bathroom malodour composition (proprietary composition of the Applicant) (c) absorbent application pads (KIMWIPES) and, (d) toilets, each in a separate testing booth of uniform dimensions.

According to the test protocol, each of the toilets were purged and flushed. Next, an absorbent pad (KIMWIPE) was placed into the bowl of each toilet. Thereafter a 3 gram aliquod of the standardized standardized liquid bathroom malodour material was placed in each of the absorbent pads and the testing booths were closed, and the toilets and booths were allowed to equilibrate for 15 minutes. Next, each of the toilets were flushed. One of the toilets and booths was untreated and used as a "control" for later comparative evaluation of malodors. To each of the other toilets was provided a sample of one of the PVOH films of E1, E2, E3, E4, C1, C2 and C3, to toilet bowls having water at 10° C.; it was observed that PVOH films of the invention dissolved in not more than 120 seconds. The toilets containing the PVOH films were allowed to equilibrate for 15 minutes. Subsequently, members (comprising 30 persons) of a trained panel evaluated each of the toilets for (a) the residual malodor perceived relative to the "control" (was assigned a reference ranking of "8" for malodor), and (b) the fragrance intensity. All rankings were on a 10 point scale where a value of "0" was indicative of no perceived fragrance, or no residual malodour perception, to a maximum value of "10" which was indicative of a "very strong" fragrance perception or residual malodour perception. The results were averaged, and are reported (at a 95% confidence level) for each of the PVOH films according to E1, E2, E3, E4, C1, C2 and C3 on the following Table 4.

TABLE 4

| | Sample | | | | | | | |
|---|---|---|---|---|---|---|---|---|
| | E1 | E2 | E3 | E4 | Control | C1 | C2 | C3 |
| (avg.) score, fragrance intensity | 3.9 | 4.3 | 4.6 | 5.3 | — | 2.7 | 1.2 | 1.7 |
| (avg.) score, residual malodour intensity | 4.5 | 3.5 | 3.3 | 3.0 | 8 | 5.9 | 8.8 | 8.3 |

As can be appreciated from the reported results, films according to the invention (example) exhibited the desirable film dissolution, fragrance delivery and malodour counteracting features desired of fast dissolving films according to the present invention. In contrast thereto, films of the comparative examples failed to provide desirable film dissolution, fragrance delivery and malodour counteracting features desired of fast dissolving films according to the present invention.

The invention claimed is:

1. A fragranced film comprising, a film formed of a water soluble and/or a water dispersible polyvinyl alcohol polymer, wherein the film comprises a fragrance constituent absorbed or adsorbed onto a free-flowing particulate material based on a polysaccharide polymer which fragrance constituent includes one or more components which individually concurrently satisfy the following parameters:
   (a) a c Log P<3.00;
   (b) a Vapor Pressure >0.1 mm Hg;
   (c) a molecular weight of <180, and
where the said components cumulatively comprise not more than about 10% wt. of the fragrance constituent.

2. The fragranced film of claim 1, wherein the polysaccharide polymer in a particulate form.

3. The fragranced film of claim 1, wherein the particulate material is microcrystalline cellulose.

4. The fragranced film of claim 1, wherein the film comprises one or more additional materials.

5. The fragranced film of claim 4, which comprises a thickener constituent.

6. The fragranced film of claim 4, which comprises an organic solvent constituent.

7. An article comprising the fragranced film of claim 1.

8. The article of claim 7, wherein the article is a pouch, sachet, or other article which further comprises one or more cleaning compositions and/or textile treatment compositions.

9. The article of claim 7, wherein the article includes as part of its construction, or alternately contains the fragranced film.

10. A method of ameliorating malodors, the method comprising the step of:
providing a fragranced film according to claim 1 to the locus of the malodors which locus also contains water in a sufficient amount to dissolve the water soluble and/or the water dispersible polyvinyl alcohol polymer of the fragranced film.

11. The fragranced film of claim 3, wherein the microcrystalline cellulose has an average particle size of between 0.01-1000 microns.

12. The fragranced film of claim 1, wherein the particulate material has a sufficiently small average particle size such that the fragrance constituent is translucent or essentially transparent within the fragranced film.

* * * * *